(12) United States Patent
Bushman et al.

(10) Patent No.: US 6,187,161 B1
(45) Date of Patent: Feb. 13, 2001

(54) REFERENCE CELL

(75) Inventors: James B. Bushman, Medina, OH (US); William P. Carlson, Hoffman Estates, IL (US); Richard E. Say, Spencer, OH (US)

(73) Assignee: Corrpro Companies, Inc., Medina, OH (US)

( * ) Notice: Under 35 U.S.C. 154(b), the term of this patent shall be extended for 0 days.

(21) Appl. No.: 07/874,745

(22) Filed: Apr. 27, 1992

(51) Int. Cl.[7] .............................. G01N 27/30; C23F 13/00
(52) U.S. Cl. ............... 204/435; 204/196.01; 204/196.06; 204/196.33; 204/196.36; 205/724; 205/727
(58) Field of Search .................................. 204/147, 148, 204/196, 197, 435, 196.01, 196.06, 196.07, 196.33, 196.36; 205/724–728

(56) References Cited

U.S. PATENT DOCUMENTS

| | | | |
|---|---|---|---|
| 2,639,265 | * 5/1953 | Simcox | 204/197 |
| 2,810,690 | * 10/1957 | Campise et al. | 204/197 |
| 3,037,926 | * 6/1962 | Ambler | 204/197 |
| 3,192,144 | * 6/1965 | Heuze | 204/435 |
| 3,725,669 | * 4/1973 | Tatum | 204/196 |
| 3,787,307 | * 1/1974 | Schwab et al. | 204/420 |
| 3,954,591 | * 5/1976 | Conkling | 204/435 |
| 4,056,446 | * 11/1977 | Vennett | 204/435 |
| 4,080,565 | * 3/1978 | Polak et al. | 204/196 |
| 4,133,732 | * 1/1979 | Boeke | 204/419 |
| 4,166,021 | * 8/1979 | Ross et al. | 204/435 |
| 4,758,324 | * 7/1988 | Winneti et al. | 204/435 |

\* cited by examiner

*Primary Examiner*—T. Tung
(74) *Attorney, Agent, or Firm*—Renner, Otto, Boiselle & Sklar

(57) ABSTRACT

An integrated cell and the test station is disclosed in a unitary package which includes internally encapsulated wiring connections at both the cell and test station. The cell and test station are tethered together by a flexible bungee tube which can be coiled and which can elongate or contract. The flexible tube provides a variable length and wide lateral flexibility. The tube also provides a convenient means to encapsulate the connections at both the cell and test station. The cell has a unique core formed by a double junction ceramic capsule. A pure copper coil element is positioned in the capsule in a super saturated solution of copper sulphate, for example. The capsule is sealed and the coil or element is electrically connected to a lead extending through the tube, and the end of the tube is encapsulated sealing the connection. The capsule is joined to one end of the bungee tube and the entire end is embedded in a stabilized hygroscopic gel which contains additional salt crystals. The entire cell end of the tube is contained in a microporous filter bag, which is in turn secured to the lower end of the tube. The test station comprises a section of rigid plastic tube with a slightly domed cap. Brass rivets are recessed in the top of the dome and connected to appropriate wiring inside the dome. The interior of the test station is then encapsulated fully sealing the wiring connections, and connecting the rigid tube to the bungee tube.

30 Claims, 2 Drawing Sheets

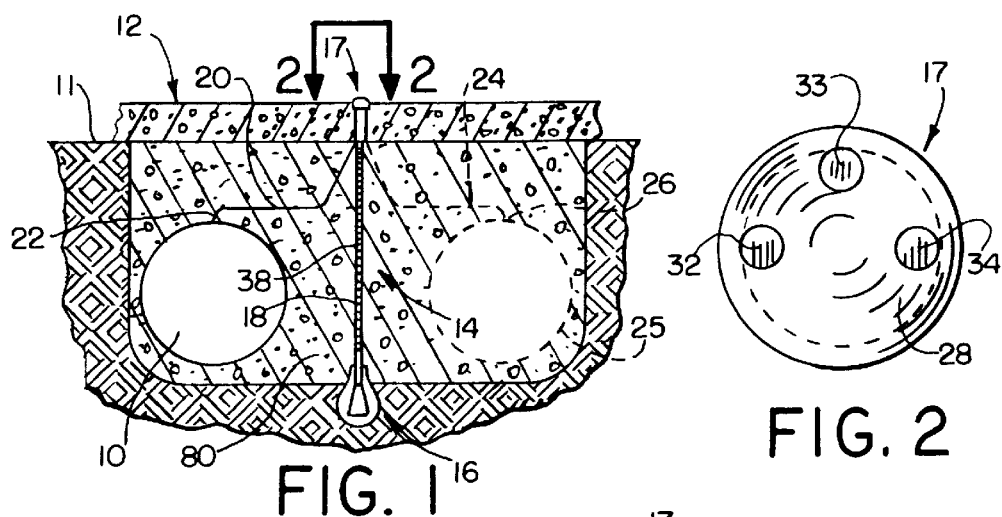
FIG. 1
FIG. 2
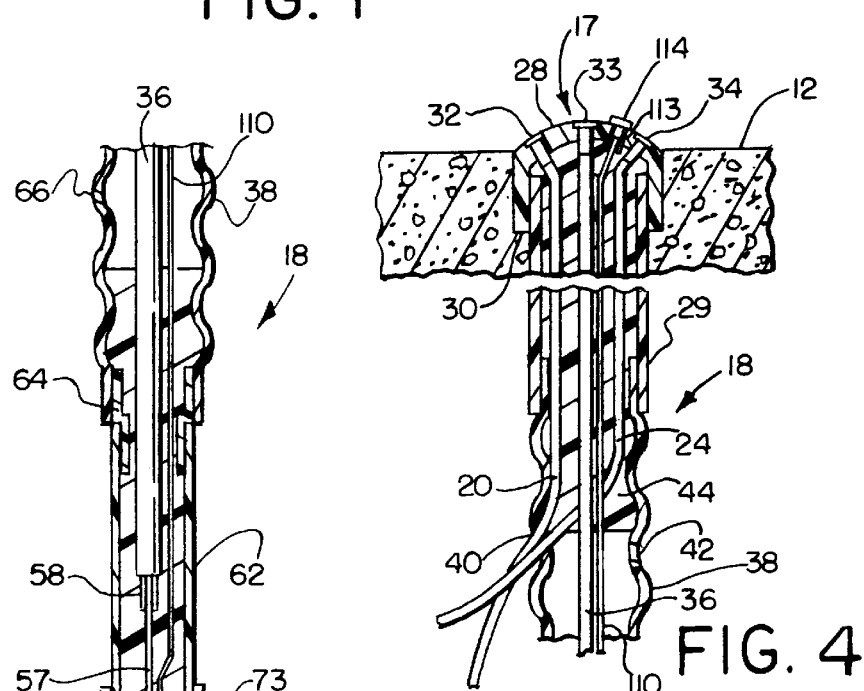
FIG. 4
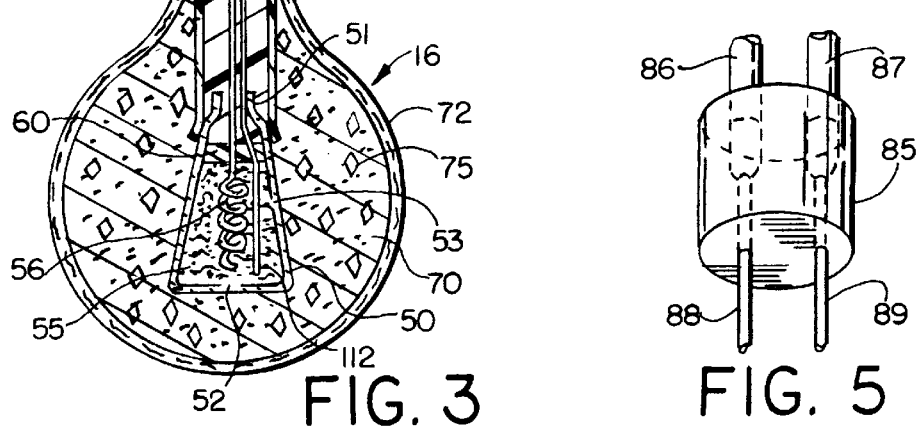
FIG. 3
FIG. 5

REFERENCE CELL

This invention relates generally as indicated to a reference cell and more particularly to a reference cell-test station combination, prepackaged, assembled, and tested, for installation as a unit.

BACKGROUND OF THE INVENTION

Cathodic protection systems may be monitored by permanent or portable reference cells. Portable reference cells may provide readings of questionable reliability since the results are dependent on a variety of factors such as cell placement and surface soil conditions. It requires an experienced and skilled technician to obtain reasonably reliable readings.

A permanent reference cell is more reliable but requires installation in the ground or electrolyte spaced from the buried or submerged structure. The cell is connected to a test station which must be accessible, i.e. normally above ground or not submerged. The test station is also electrically connected to the structure enabling the potential measurement to be taken conveniently at the test station.

A permanent reference cell must have a long design life and be relatively easy to install. Moreover, the installation procedure should itself avoid damage to the cell or test station. The test station should also be simple and easy to use. Over a long design life, the test station may itself be subject to corrosion, or more likely vandalism if caps can be removed or doors opened to provide access to the particular wiring connections. This is particularly true if the wiring connections provide movable or removable parts such as binding posts or even banana jacks.

Conventionally, an installing contractor orders a reference cell, a test station or terminal box, and sufficient wire to connect the cell to the test station and the test station to the buried structure or structures. The wiring connections are done in the field at what is usually a major construction site involving excavation, excavation machinery, backfills, backfill machinery and sometimes the removal and installation or replacement of pavement. This is all usually accomplished in an environment of mud or dirt. Before the system is backfilled, the system is tested. Complete aggravation results when the system is tested after installation and backfill and fails to work properly. Failure most often occurs at the electrical connections which are made in the field and subject to the visits of a construction site. Examples of cells commercially available are a variety of cells sold under the trademark PERMACELL® by Harco Corporation of Medina, Ohio. These include underground copper-copper sulphate, or silver-silver chloride cells, and silver-silver chloride cells for salt water applications. A variety of test stations are also available usually requiring removable caps, doors, etc., and binding post or banana jack wiring connections.

SUMMARY OF THE INVENTION

The present invention integrates an improved cell and the test station in a unitary package which includes internally encapsulated wiring connections at both the cell and test station. The cell and test station are tethered together by a flexible bungee tube which can be coiled and which can elongate or contract. The flexible tube integrates the two units at each end yet provides a variable length and wide lateral flexibility. The tube also provides a convenient means to encapsulate the connections at both the cell and test station.

The cell comprises a unique canister or core formed by a double junction ceramic capsule. A pure copper coil element is positioned in the capsule in a super saturated solution of copper sulphate, for example. The capsule is sealed and the coil or element is electrically connected to a lead extending through the tube, and the end of the tube is encapsulated sealing the connection. The capsule is joined to one end of the flexible tube and the entire end is embedded in a stabilized hygroscopic thixotropic gel which contains additional salt crystals. The entire cell end of the tube is contained in a durable geotextile microporous filter bag, which is in turn secured to the lower end of the tube. The cell end is sealed in a plastic bag until ready for use.

The test station comprises a section of rigid plastic tube with a slightly domed cap. The length of the rigid plastic tube may vary depending on whether the test station is flush or post mounted. Brass rivets are recessed in the top of the dome and connected to appropriate wiring inside the dome. The interior of the test station is then encapsulated fully sealing the wiring connections.

The brass rivets or buttons are placed on the dome so that a reading may quickly be taken by a two-prong test probe. If more than one buried or submerged structure is being monitored, the spacing is such that structure-to-structure potentials cannot be read by mistake.

The slightly domed top surface of the test station enables it to be mounted flush with pavement. The material is a tough ultraviolet resistant plastic which can withstand vehicle traffic and wear. The dome configuration elevates the contacts above ponding which may occur on pavement after or during inclement weather. This reduces the probability of corrosion of the contacts.

Optionally the test station and cell may be interconnected by a small plastic tube so that the cell may be replenished, and so that test measurement may be made through the tube, acting as a salt bridge. Both the interconnecting lead and the small plastic tube, if used, may be slightly coiled in the flexible tube so that even maximum elongation of the tethering flexible tube will put no tension on the lead wire or its connections. The flexible tube may be corrugated, such corrugations acting to protect the lead inside, while providing greater axial elongation.

It is a principal object of the present invention to provide a totally integrated cell and test station system which is complete with a test station, wiring, and a permanent reference cell which has a long design life. More importantly, the cell-test station combination can readily be factory fabricated and tested, coiled for shipment, and readily installed at the construction site without requiring field electrical connections, other than those connecting the test station to the structure, or other field fabrications or manipulations which can adversely affect the performance and life of the installation.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

In said annexed drawings:

FIG. 1 is a vertical section on a substantially reduced scale of the present invention being installed in connection with an underground tank, or optionally two tanks, the latter being shown in dotted lines;

FIG. 2 is an enlarged top view of the top of the test station which is flush mounted with the pavement in FIG. 1;

FIG. 3 is an enlarged vertical section through the cell end of the integrated system;

FIG. 4 is an enlarged vertical section through the test station of the integrated system;

FIG. 5 is an enlarged perspective view of a test probe which may be used in conjunction with the test station contacts seen in FIG. 2;

DETAILED DESCRIPTION OF THE PREFERRED EMBODIMENTS

Figure 6:
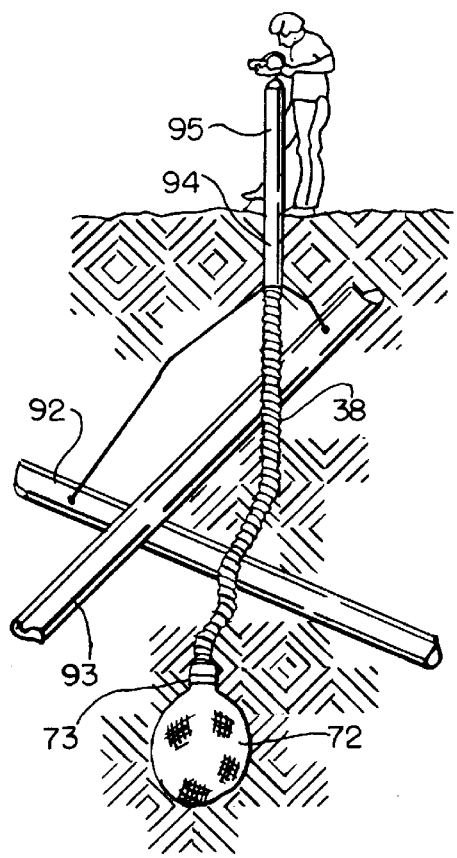
FIG. 6 is a schematic illustration of an application being utilized to monitor two crossing buried pipes, with the test station being a post mount rather than a flush mount.

Referring first to FIG. 1 there is illustrated a metal tank 10 buried beneath surface 11 and pavement 12. The cell-test station system of the present invention is shown generally at 14 and comprises a reference cell 16, a test station 17, and an interconnecting flexible tube 18 which tethers the test station and cell together. The test station and cell are electrically connected inside the tube, and the test station is electrically connected to the tank 10 by the lead 20. The lead 20 may be electrically connected to the tank 10 at 21 by a coated thermite connection indicated at 22. If two tanks are to be monitored by the reference cell, a second lead indicated by the dotted lines seen at 24 is provided connecting the second tank 25 through coated thermite connection 26 to the test station.

Referring now to FIG. 4 it will be seen that the test station 17 includes a somewhat domed cap 28 which telescopes over a section of rigid plastic tube indicated at 29. The length of the tube 29 may vary as hereinafter described depending upon whether the test station is flush mounted or post mounted. When telescoped in position and properly encapsulated the cap provides an annular significant shoulder indicated at 30. The cap includes a domed top surface as illustrated which projects somewhat above the surface of pavement 12. Inserted in the test station cap are brass rivets indicated at 32, 33 and 34. These rivets include a flat head or contact surface which is flush with the exterior surface of the cap and also include a shank projecting inwardly through the cap. The shank is hollow and facilitates the securing thereto of the respective leads 20, 36, and 24. Connected to the lower end of the rigid pipe section 29 is the upper end of a corrugated flexible tube 38. The two leads 20 and 24 which are connected from the test station to the respective tanks 10 and 25 exit the tube 38 through a lateral hole indicated at 40. The lead 36 continues through the flexible tube 38 to connect to the cell shown in detail in FIG. 3.

In practice, the insulated wires or leads are threaded through the flexible tube with the rigid pipe section on the end thereof. After the wires are electrically secured to the shanks of the brass rivets as by crimping or soldering, the rigid pipe section is telescoped into the cap. The entire assembly is then turned upside down and then through a lateral hole, such as indicated at 42, the now entire lower end is filled with epoxy or other suitable potting compound as indicated at 44. The epoxy completely fills the entire end of the test station and when cured secures the pipe 29 to the cap, and the flexible tube 38 to the pipe 29. It also secures the electrical wires in place and more importantly encapsulates and seals the electrical connections in the interior of the test station cap.

Referring now to FIG. 3 there is illustrated the normally lower end of the reference cell-test station combination. The core of the reference cell is a ceramic canister or capsule indicated at 50. The capsule is slightly larger at the bottom than at the top, the top being provided with a necked opening indicated at 51. The ceramic capsule is provided with a glazed coating or surface both inside and out except for a small central interior port indicated at 52 and a lateral exterior elevated port indicated at 53. The canister is filled with a copper-copper sulphate slurry or paste seen at 55 and a copper coil or wire is embedded in the paste as seen at 56. The coil is preferably 99.9 percent pure copper. The coil includes a vertically projecting wire 57 which extends upwardly through the neck 51. The wire 57 is electrically connected at 58 to the lower end of the insulated lead 36. After the wire is in position, the copper-copper sulphate paste is sealed in the canister by a layer of epoxy indicated at 60. A plastic tube seen at 62 is fitted tightly over the smaller upper end of the ceramic capsule with the opposite or upper end fitting over the reduced projecting end of hose fitting 64 which is secured to the lower end of the flexible tube 38.

When the connection is made between the ceramic capsule and the lower end of the flexible tube, with the electrical connection 58 in place, liquid epoxy or potting compound is then introduced into the flexible tubing through a lateral port such as seen at 66 which then fills the entire lower end of the flexible tubing, including the tube 62. When the liquid plastic material or potting compound cures or solidifies as indicated at 68, the flexible tube is firmly secured to the tube 62, and the tube 62 to the top of capsule 50. The epoxy sealant or potting compound may be the same material used to form the seal 60. When the compound cures the ceramic capsule is firmly secured to the lower end of the flexible tube and the solder or crimp connection 58 is completely encapsulated and sealed. For more detail of the ceramic capsule and how it is made, reference may be had to the copending application of William Carlson filed Aug. 1, 1991, Ser. No. 07/739,193 entitled "Electrode", now U.S. Pat. No. 5,370,783.

The ceramic capsule is surrounded by a thixotropic gel indicated at 70 which is contained in a microporous, relatively thick geotextile filter bag indicated at 72 which is securely tied around the tube 62 by the tight plastic tie 73, above the ceramic capsule 50. The thixotropic gel may be a moist form of clay and is hygroscopic. Embedded uniformly within the clay or thixotropic gel are copper sulphate crystals indicated at 75. The microporous filter bag full of the hygroscopic material may, if desired, be shipped separately with the ceramic capsule end of the cell, being inserted into the bag at the installation site. The bag may be sealed tightly to prevent any drying out prior to installation. If the bag is installed on the cell end of the cell-test station, it should also be securely sealed with a plastic bag or wrapping to prevent drying out before installation. Of course, prior to installation the plastic bag must be removed.

The employment of copper sulphate crystals in the stabilized thixotropic gel greatly enhances the design life of the cell since it may be many years before the copper sulphate within the ceramic capsule begins to leach away. The copper sulphate crystals outside the capsule act as a retardant significantly slowing the process which reduces the design life of the cell. The one interior and offset exterior port and the glazing of the ceramic capsule provide a significant baffled path for ion flow, and what may be termed a double junction between the contents of the capsule and the surrounding electrolyte. This greatly enhances the design life of the cell.

Reverting back to FIG. 1 it will be seen that a select backfill indicated at 80 may be positioned around the tanks but that a native soil backfill is preferred around the reference cell.

Referring now to FIG. 5 there is illustrated a special probe 84 which may be employed with the test station conveniently to obtain the required readings. The probe comprises a molded plastic grip 85. From one end project the insulated leads 86 and 87 leading to the meter. From the opposite end project contact prods 88 and 89. The contact prods are of course connected through the wires to the meter. The contact prods are spaced to enable one to take a reading between the contact points 32 and 33, or 33 and 34, as seen in FIG. 2, but not 32 and 34. While the test station will normally have proper marking or raised identification showing the proper contacts to be made, after decades of use the markings may wear off. Accordingly the spacing of the contact probe prevents the incorrect reading from being obtained.

Referring now to FIG. 6 there is illustrated another installation where the combination cell and test station is buried adjacent crossing pipes seen at 92 and 93. The only difference is that the pipe indicated at 94 is somewhat longer so that the pipe and test station project above the ground forming a post 95. The top of the test station is otherwise identical to the test station seen in FIG. 1.

Although the ceramic capsule cell has a very long design life, it may nonetheless be desired to be able to replenish that cell from the test station. It also may be desirable to take certain measurements of the cell from the test station and for that reason it may be desirable to connect the interior of the ceramic capsule to the test station through an elongated plastic tube. This plastic tube which may optionally be employed is illustrated in FIGS. 3 and 4 at 110. At the bottom the plastic tube terminates near the bottom of the ceramic canister or capsule as seen at 112. At the top the tube fits within a fitting 113 which may be closed by a plug 114. The interior of the tube may be provided with a wick, in this manner additional salt solution may be provided to the ceramic capsule and certain electrical measurements may be made using the salt solution in the tube as a salt bridge. The inclusion of the tube is optional and it can be installed at the same time as the insulated lead 36.

Figure 7:
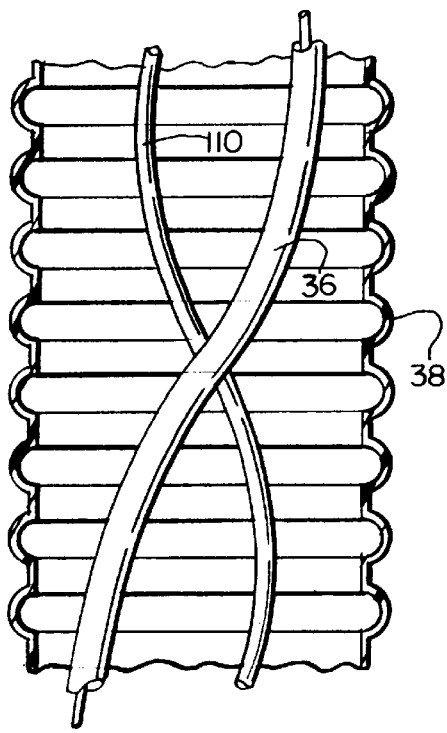
FIG. 7 is an enlarged axial section through the flexible tethering tube illustrating how the lead and small flexible tube may be slightly coiled to preclude tensile forces thereon.

Referring now to FIG. 7, since the flexible tube 38 is quite capable of axial expansion and contraction, the lead 36 and the small tubing 110 within such flexible tubing will be slightly coiled so that even at the maximum axial elongation of the flexible tube tether, no axial tension will be placed on either the tube or the lead. The flexible tube and the ribs thereof act physically to protect the lead and the interior tube, primarily from abrasion which might result in the shipment and installation process.

The system of the present invention utilizes schedule 80 ultraviolet and chemically resistant PVC piping and solid brass contact points which are encapsulated to the wiring for a truly sealed connection. The recessed contact points are readily accessible and positioned to reduce operator error with no caps to remove or loose or awkward fittings to deal with.

To protect against damage from chemicals found in buried environments, insulated copper wire is used to connect the test station to the reference cell. The flexible tubing covers this wire and prevents wire damage during installation while also providing greater flexibility for greater cell placement options as seen for example in FIG. 6. The cell may be substantially vertically and laterally offset from the test station.

The supersaturated copper sulphate solution within the cell is prevented from easily exiting and mixing with ground fluids by the double junction ceramic cup. An inside track within the cup allows the saturated solution to make external contact through an internal port which is greatly separated from the external port or ports. Surrounding the entire cell is an electrically conductive thixotropic stabilized gel backfill which is contained around the cell by a semipermeable microporous geotextile membrane. The gel guarantees a moist environment for the cell and thus accurate potential readings.

Figure 8:
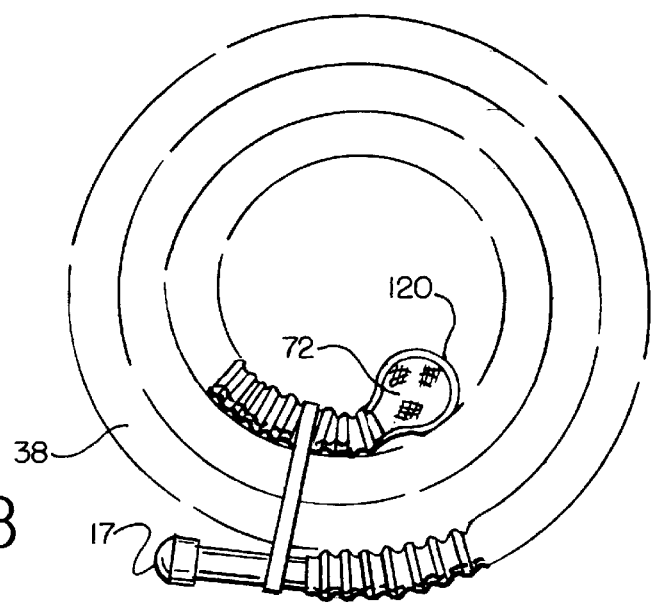
FIG. 8 is an illustration of how the system may be coiled for packaging and shipment.

The system is adapted for a wide variety of buried or submerged steel structures. Test stations can be selected for either post or flush mounting, with a six foot post, such as seen in FIG. 6, or an eight inch long flush mount station, such as seen in FIG. 1. Overall lengths between the test station and the cell may vary, for example, anywhere from three to twenty-four feet or more. Special lengths of course can also be fabricated. For longer lengths, the cell and test station may be coiled into a compact package as seen for example in FIG. 8. This package may be bundled together and shipped much as a swimming pool hose or a vacuum hose for quick installation at the site. The cell is covered by a plastic bag 120 to keep the cell from drying out. It must be removed before installation. In any event the cell provides easy field installation, protection from the harsh environment of a construction site, and the surety of factory made and sealed wire connections.

While in some buried soil situations, the copper-copper sulphate solid salt slurry is preferred, it will readily be appreciated that other solid salt slurries may more advantageously be used in other situations. For example, the silver-silver chloride or mercury-mercury chloride calomel elements may be employed. Composition salt is typically potassium chloride or potassium nitrate. However many other equitransferent salts are also suitable.

Although the invention has been shown and described with respect to a preferred embodiment, it is obvious that equivalent alterations and modifications will occur to others skilled in the art upon the reading and understanding of this specification. The present invention includes all such equivalent alterations and modifications, and is limited only by the scope of the claims.

What is claimed is:

1. In combination, a reference cell and test station for buried metal structures, said test station and cell being physically interconnected together by a flexible tether tube, said tube being capable of axial contraction and extension, an electrical lead interconnecting said cell and test station through said tube, said lead being longer than the maximum extension of the tube whereby any tension on said electrical lead is avoided, and wherein each electrical connection of said lead is encapsulated.

2. The combination set forth in claim 1 wherein said tube is corrugated.

3. The combination set forth in claim 1 wherein said tube has sufficient lateral flexibility that it may be coiled for shipment of said combination as a unit.

4. The combination of claim 1 wherein said test station is a rigid tube extension of said tether tube, said rigid tube having external contact points.

5. The combination set forth in claim 4 wherein said external contact points are on a slightly domed end surface of said rigid tube.

6. The combination set forth in claim 5 wherein said contact points are spaced to match the spacing of a test probe.

7. The combination of claim 1 wherein said cell is connected to one end of said tether tube, and comprises a ceramic capsule containing a saturated salt solution with a conductive element therein electrically connected to said lead.

8. The combination set forth in claim 7 wherein said capsule includes an electrical path through the wall of the capsule for external contact, the internal and external ends of said path being offset.

9. The combination set forth in claim 8 wherein said ceramic capsule is surrounded by a thixotropic gel in a geotextile filter.

10. The combination set forth in claim 9 including additional salt crystals mixed in the gel.

11. The combination set forth in claim 1 wherein the encapsulation of each electrical connection also serves mechanically to connect each end of the flexible tether tube to the test station and cell, respectively.

12. A reference cell and test station combination for buried or submerged metal structures comprising an elongated conduit, an ion permeable cell exposed at one end of said conduit but connected and sealed with respect thereto, and a test station at the other end, an electrical lead extending from said cell to said test station through said conduit, and at least one additional lead extending from said test station, at least partly through said conduit, and adapted to be connected electrically to a metal structure, said conduit, cell, test station, and leads being prepackaged for installation as a unit.

13. A combination as set forth in claim 12 wherein said conduit is a flexible tube.

14. A combination as set forth in claim 13 wherein said test station comprises a rigid tube extension of said flexible tube, said rigid tube having external contact points.

15. The combination set forth in claim 14 wherein said external contact points are on a slightly domed end surface of said rigid tube.

16. The combination set forth in claim 14 wherein said contact points are spaced to match the spacing of a test probe.

17. A combination as set forth in claim 16 wherein said contact points have internal electrical connections and said internal electrical connections to said contact points are encapsulated.

18. A combination as set forth in claim 13 wherein said cell is connected to one end of said flexible tube and comprises a ceramic capsule containing a saturated salt solution with a conductive element therein.

19. The combination set forth in claim 18 wherein said capsule includes an electrical path through the wall of the capsule for external contact, the internal and external ends of said path being offset.

20. The combination set forth in claim 19 wherein said ceramic capsule is surrounded by a thixotropic gel in a geotextile filter.

21. The combination set forth in claim 20 including additional salt crystals mixed in the gel.

22. A reference cell comprising a ceramic capsule containing a saturated salt solution, a conductive wire in said solution and extending from said capsule, a flexible tube having one end connected to said capsule through a reduced tubular fitting, said wire being connected to a lead in said tube, said wire-lead connection being encapsulated in plastic, and said encapsulating plastic firmly securing said tube to said capsule.

23. A test station comprising a rigid tube adapted to project at least partly from an electrolyte, electrical leads within said tube extending to a buried or submerged structure and a reference cell respectively, electrical contact points projecting through said tube and internally connected to said leads, said internal connections being totally encapsulated.

24. A test station as set forth in claim 23 wherein said contact points are on a domed end of said tube, with the entire domed end being filled with a potting compound to encapsulate said connections.

25. A test station as set forth in claim 24 wherein said contact points are formed by rivets flush with the surface of the dome.

26. A test station as set forth in claim 23 wherein said contact points are spaced to match the spacing of a test probe.

27. A test station as set forth in claim 23 including a flexible conduit connecting said test station to said cell.

28. A test station as set forth in claim 27 wherein said encapsulation secures said tube to said flexible conduit.

29. A cell for measuring the electrical potential of structures buried in electrolyte comprising an electrolyte exposable cell, a test station adapted to project above the surface of the electrolyte and providing readily accessible test reading terminals, said test station and cell being tethered together by a bungee tube, said bungee tube including an electrical lead extending therethrough, and connected at each end to said cell and test station respectively, each connection being encapsulated within the tube.

30. A cell as set forth in claim 29 wherein said bungee tube is a corrugated hollow tube, and said electrical lead being coiled within said bungee tube to avoid tension on said electrical lead as said bungee tube elongates.

\* \* \* \* \*